United States Patent
Kuk et al.

(10) Patent No.: US 9,265,420 B2
(45) Date of Patent: Feb. 23, 2016

(54) METHOD OF AUDITORY TRAINING AND A HEARING AID SYSTEM

(71) Applicant: Widex A/S, Lynge (DK)

(72) Inventors: Francis Kok-Ming Kuk, Lynge (DK); Petri Mikael Korhonen, Lynge (DK)

(73) Assignee: Widex A/S, Lynge (DK)

( * ) Notice: Subject to any disclaimer, the term of this patent is extended or adjusted under 35 U.S.C. 154(b) by 130 days.

(21) Appl. No.: 14/132,370

(22) Filed: Dec. 18, 2013

(65) Prior Publication Data

US 2015/0172838 A1 Jun. 18, 2015

(51) Int. Cl.
*H04R 25/00* (2006.01)
*A61B 5/00* (2006.01)
*G06F 19/00* (2011.01)

(52) U.S. Cl.
CPC ............... *A61B 5/00* (2013.01); *H04R 25/558* (2013.01); *G06F 19/3481* (2013.01)

(58) Field of Classification Search
CPC ........ G02C 11/06; H04M 3/005; H04M 3/02; H04M 19/02; H04M 19/023; H04M 19/04; H04R 25/00; H04R 25/30; H04R 25/70; H04R 25/305; H04R 25/356; H04R 25/505; H04R 25/552; H04R 25/554; H04R 25/558; H04R 25/606; H04R 2225/41; H04R 2460/13
USPC ..................... 381/312, 315, 23.1, 60; 607/57; 379/418
See application file for complete search history.

(56) References Cited

U.S. PATENT DOCUMENTS

| | | | |
|---|---|---|---|
| 2004/0194610 A1* | 10/2004 | Davis | 84/466 |
| 2011/0280409 A1* | 11/2011 | Michael et al. | 381/60 |
| 2012/0219159 A1* | 8/2012 | Burk et al. | 381/60 |

OTHER PUBLICATIONS

Christian Kaernbach "A single-interval adjustment-matrix (SIAM) procedure for unbiased adaptive testing", J. Acoust. Soc. Am 88 (6), Dec. 1990, pp. 2645-2655.
H. Levitt, "Transformed Up-Down Methods in Psychoacoustics", The Journal of the Acoustical Society of America, vol. 49, No. 2 1971, pp. 467-477.
Alexandra Parbery-Clark et al, "Musician Enhancement for Speech-In-Noise", Ear& Hearing, vol. 30, No. 6, pp. 653-661 2009.
Claudia Lappe et al, "Cortical Plasticity Induced by Short-Term Unimodal and Multimodal Musical Training", The Journal of Neuroscience, Sep. 24, 2008, pp. 9632-9639.
Robert W. Sweetow et al, "Warning: Do Not Add on Aural Rehabilitation or Auditory Training to Your Fitting Procedures", Hearing Review Jun. 2007 from 2007 Clinical Research Summit.
Takako Fujioka et al, "One year of musical training affects development of auditory cortical-evoked fields in young children", Brain (2006), 129, pp. 2593-2608.

* cited by examiner

*Primary Examiner* — Brian Ensey
(74) *Attorney, Agent, or Firm* — Sughrue Mion, PLLC

(57) ABSTRACT

A method of auditory training for hearing impaired persons, wherein a trainee is prompted to arrange a set of melodies based on a musical feature shared by some of the melodies, a hearing aid system (100), and a computer-readable storage medium having computer-executable instructions adapted to carry out a method of auditory training.

14 Claims, 7 Drawing Sheets

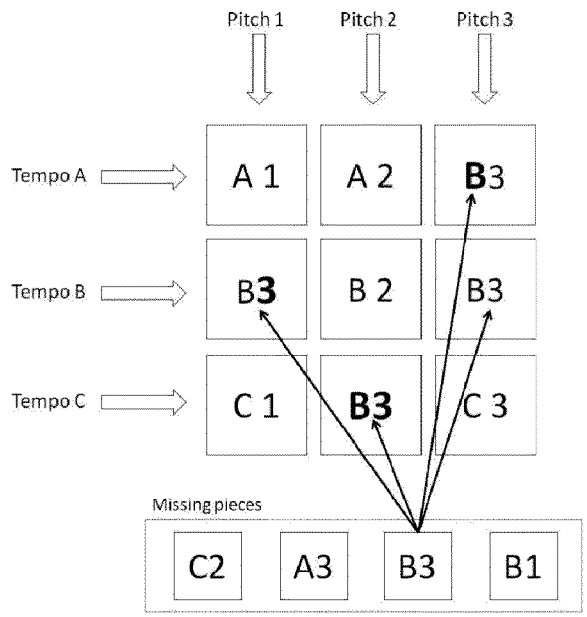
*Figure 10*
*Figure 11*            *Figure 12*

METHOD OF AUDITORY TRAINING AND A HEARING AID SYSTEM

BACKGROUND OF THE INVENTION

1. Field of the Invention

The present invention relates to a method of auditory training. The invention also relates a hearing aid system configured to carry out a method of auditory training. Furthermore the invention relates to a computer-readable storage medium having computer-executable instructions carrying out the method when executed in a personal communication device.

Generally a hearing aid system according to the invention is understood as meaning any system which provides an output signal that can be perceived as an acoustic signal by a user or contributes to providing such an output signal and which has means which are used to compensate an individual hearing loss of the user or contribute to compensating the hearing loss of the user or contribute to compensating the hearing loss. A binaural hearing aid system always consists of two hearing aids, one for each ear of the hearing aid user.

Furthermore, auxiliary devices whose main aim is not to compensate for a hearing loss, for example consumer electronic devices (smart phones, tablet computers, personal digital assistants (PDAs), MP3 players, televisions, hi-fi systems etc.) may also be considered part of a hearing aid system, provided they have measures for compensating an individual hearing loss or measures for controlling the operation of a hearing aid.

Within the present context a hearing aid can be understood as a small, battery-powered, microelectronic device designed to be worn behind or in the human ear by a hearing-impaired user. Prior to use, the hearing aid is adjusted by a hearing aid fitter according to a prescription. The prescription is based on a hearing test, resulting in a so-called audiogram, of the performance of the hearing-impaired user's unaided hearing. The prescription is developed to reach a setting where the hearing aid will alleviate a hearing loss by amplifying sound at frequencies in those parts of the audible frequency range where the user suffers a hearing deficit. A hearing aid comprises one or more microphones, a battery, a microelectronic circuit comprising a signal processor configured to provide said amplification, and an acoustic output transducer. The signal processor is preferably a digital signal processor (DSP). The hearing aid is enclosed in a casing suitable for fitting behind or in a human ear.

Thus within the present context the term "hearing aid system device" may denote a hearing aid or an auxiliary device.

Auxiliary devices such as e.g. remote controls, smart phones and tablet computers adapted for use with hearing aids are known. They offer a convenient way of operating various user-accessible features of a hearing aid such as volume level and program selection.

Hearing aid systems can compensate for compromised audibility and provide frequency dependent amplification. However, it may be difficult for the hearing aid system to fully compensate all the difficulties that hearing impaired users face due to their limited frequency resolution, impaired temporal processing, maladaptive listening strategies and changes in cognitive function. These skills can however be enhanced with training.

Despite the documented benefit of training, several reports have shown that less than 10% of audiologists offer comprehensive auditory training to patients with hearing impairment, the reasons for the reluctance to offer training is described in the article: "WARNING: Do NOT Add On Aural Rehabilitation or Auditory Training to Your Fitting Procedures", by Sweetow and Henderson Sabes in Hearing Review June 2007, from the 2007 Clinical Research Summit.

Even with training from the audiologist, the training is often not sufficient, because the hearing impaired is unwilling to spend more than a few visits at the audiologist being trained. Thus the offer, from the audiologist, to train the hearing impaired is often refused by the hearing impaired because of the inconvenience of going to the audiologist. To benefit optimally from the hearing training, the training sessions should be followed regularly. Several computer programs working as stand alone, or in a network using e.g. the internet, have been proposed, hereby offering training for the hearing impaired at home.

2. The Prior Art

EP 1912476 B1 discloses a method of training auditory skills of a hearing aid user by means of the following steps performed by a hearing aid: presenting a sound sample, recording and analyzing the response of the hearing aid user to the sound sample, and repeating the training step multiple times, including the steps of presenting different sound samples as well as recording and analyzing within the framework of a training session, and by means of the step of providing feedback, related to the progress in the training success, to the hearing aid user. However, the publication is silent with respect to how the response of the hearing aid user is recorded and evaluated.

A number of computer-assisted auditory training software programs have been proposed, e.g. CASPERSENT, CAST, LACE, etc. These programs include exercises to facilitate the improvement of auditory skills using natural or processed (e.g. frequency filtered or time compressed) speech, environmental sounds, pure tones, or music. These exercises can typically be performed in quiet or in the presence of competing noise.

While these programs provide a convenient and effective means to provide auditory training, there are situations where these existing computer programs do not suffice. First, these programs use speech as part of the training, which render them language-dependent, and the development cost of such a training program can be a major obstacle in language regions where the number of patients potentially benefitting from the program is small. Second, these programs require recording of natural speech as a stimulus. Natural speech is a logical choice when the goal of the training is to improve speech-in-noise performance. However, the selection of the natural speech to be used as stimulus can be a tedious undertaking. Also, the recording of the stimuli can be a time consuming task. Third, depending on the design of the training program, the trainee may find the training tedious and unexciting. More entertaining training programs have been shown to reduce dropout rates, and to improve effectiveness of auditory training.

It is therefore a feature of the present invention to provide a more efficient, reliable and entertaining method of providing auditory training and to provide a hearing aid system for training the auditory skills of a hearing impaired user.

SUMMARY OF THE INVENTION

The invention in a first aspect provides a method of auditory training, comprising the steps of: providing in a graphical user interface a first arrangement comprising a first, second and third box positioned at a first, second and third location respectively, wherein said graphical user interface is adapted to enable a user to activate a box, to launch the playing of an auditory sequence of notes from a musical scale, and wherein said graphical user interface is adapted to enable a user to select, and move and drop a box, prompting the user to rearrange the location of at least one box, wherein said first, second and third boxes are configured such that they share a musical characteristic, wherein said musical characteristic is selected from a group comprising the selected notes from a musical scale, the type of instrument used to provide the notes, the sequential order of the notes and the duration of the notes, and wherein the graphical appearance of said boxes is adapted such that re-arrangement by the user will require the user to activate said boxes, and listen to the provided auditory sequences to identify sound patterns distinguishing the boxes, to consider similarities of the sound patterns and to move a box into a position where the sound pattern of the box shares similarities with the sound patterns of the neighboring boxes.

The invention in a second aspect provides a hearing aid system comprising a hearing aid and a graphical user interface, said graphical user interface providing a first arrangement comprising a first, second and third box positioned at a first, second and third location respectively, wherein said graphical user interface is adapted to enable a user to activate a box to launch the playing by said hearing aid of a respective auditory sequence of notes from a musical scale, wherein said graphical user interface is adapted to enable a user to select, and move and drop a box, wherein each of said first, second and third boxes is associated with a particular auditory sequence, the respective auditory sequences being distinguished, yet sharing some musical characteristics, in order to suggest to the user a meaningful ranking among the boxes in accordance with the auditory sequences, said musical characteristics being selected from a group comprising selected notes from a musical scale, type of musical instrument used to provide the notes, sequential order of the notes and duration of the notes, and wherein the graphical user interface is adapted to prompt the user to activate said boxes to play respective auditory sequences, to listen to the auditory sequences, to compare sound patterns of respective auditory sequences and consider rankings among them, and to move at least one box into a position where auditory sequences of neighboring boxes together provide a meaningful pattern.

The invention in a third aspect provides a computer-readable storage medium having computer-executable instructions, which when executed in a personal communication device provides auditory training of a hearing impaired person, comprising the steps of: providing in a graphical user interface a first arrangement comprising a first, second and third box positioned at a first, second and third location respectively, wherein said graphical user interface is adapted to enable a user to activate a box, to launch the playing of an auditory sequence of notes from a musical scale, and wherein said graphical user interface is adapted to enable a user to select, and move and drop a box, prompting the user to re-arrange the location of at least one box, wherein said first, second and third boxes are configured such that they share a musical characteristic, wherein said musical characteristic is selected from a group comprising the selected notes from a musical scale, the type of instrument used to provide the notes, the sequential order of the notes and the duration of the notes, and wherein the graphical appearance of said boxes is adapted such that re-arrangement by the user will require the user to activate said boxes, and listen to the provided auditory sequences to identify sound patterns distinguishing the boxes, to consider similarities of the sound patterns and to move a box into a position where the sound pattern of the box shares similarities with the sound patterns of the neighboring boxes.

Musical notes for stimulus signals can be used in all language regions. Relying on such sounds for training greatly simplifies any local adaptations. Further the inventor has found that training with musical sounds can be effective and reliable as well as entertaining, and that the user needs not be skilled in musical appreciation.

Traditional music training has been shown to induce structural and functional changes in the auditory system. Studies have demonstrated that musicians' brains have increased gray matter in auditory cortices, Broca's area, the left primary sensorimotor cortex, right cerebellum, visuo-spatial areas, and the hippocampus. Studies on functional changes have revealed that musicians' brain responses are larger than non-musicians' to piano tones, to their own instrument, and even to artificial tones. Interestingly, musical training can also improve auditory skills that are not exclusively related to music Skills of musicians acquired through years of training are used in domains, such as speech, language, emotion, and auditory processing.

As one example, musicians' brains show a more robust and faithful encoding of the pitch information contained in speech sound in subcortical levels of auditory pathway. Most importantly, musical training has been shown to enhance the ability to hear speech in challenging listening environments. Musicians are experts in extracting relevant auditory signals from the complex soundscapes such as an orchestra. This skill has been shown to transfer to speech perception in noise. In the article "Musician enhancement for speech-in-noise" by Parbery-Clark et al in Ear and Hearing 30, no. 6 (2009): pages 653-61 clinical measures of speech perception in noise between 16 normal hearing musicians and 15 non-musicians between the ages of 19 and 31 years were compared. The performance was assessed with a so called QuickSIN test and a Hearing-In-Noise Test (HINT). Musicians outperformed the non-musicians on both the QuickSIN and the Hearing-In-Noise Test when speech and noise were presented from the same spatial location. In addition, musicians demonstrated better perceptual skills as evidenced by smaller frequency discrimination thresholds, and greater working memory capacity.

In the article "One year of musical training affects development of auditory cortical-evoked fields in young children" by Fujioka et al, in Brain (2006), 129, pages 2593-2608 it is investigated whether musicians exhibit improved auditory function due to their musical training or because they are individuals with a better auditory function and therefore more likely to engage in musical training. Fujioka et al studied brain responses of 4-6 year-old children undertaking one year of musical training. In the beginning of the training their brain responses did not differ from those of control group. However, after a year of training differences in responses to violin sound were seen between the musically trained children and the control group of untrained children.

In the article "Cortical plasticity induced by short-term unimodal and multimodal musical training" by Lappe et al, in The Journal of Neuroscience: (2008); 28 (39) it is reported that learning to play the piano over the course of 2 weeks showed enhancement in the Musically elicited Mismatch Negativity (MMN) in non-musician adult listeners. Enhancement (however smaller) was even seen with those participants who did not actively train but only listened and made judgments about the piano music.

While music and speech are perceptually different, several similarities also exist between music and speech at both the acoustic and cognitive level. At the acoustic level both music and speech use pitch, timing, and timbre as cues to convey information.

In music, pitch contours and intervals are used to communicate melodies and tone centers. In speech, pitch patterns communicate prosodic information such as the speaker's intention and emotion.

In music, timing is used to indicate rhythm and each instrument has a characteristic temporal envelope that distinguishes it from other instruments. In speech, timing is used to convey prosodic information, to indicate phonetic cues such as the release bursts of stop consonants, and is used contrastively in many languages (e.g. long and short vowels).

Concerning timbre, each musical instrument and even playing style has a unique timbre that defines the tone of the instrument. In speech, timbre is used to define speech formats, which establish the phonetic identities of speech sounds.

At the cognitive level both music and speech processing involve high working-memory load, selective attention skills, and implicit learning of the acoustic and syntactic rules that integrate discrete events to a perceptual stream. Similar to all human languages in which sentences are composed of words in a certain linear order, musical phrases are composed of notes in a non-random order. The specific order of notes can for example alter the expectations of a melody from resolved to unresolved. During musical training the acoustic and cognitive skills required from a successful musician are enhanced through years of active engagement with the fine-grained acoustics of music. These acquired skills have been shown to result in enhanced processing of speech and language.

Embodiments of the invention may provide the user with sounds of musical instruments. A multitude of melodic sequences (i.e. a sequence of notes from a single instrument e.g. a piano, guitar, flute, or a musical instrument synthesizer) can be used to challenge the user to recognize a given relationship in the presented melodic sequences using problem solving skills The perceptual similarities of the melodic sequences are iteratively adjusted based on the user's performance to provide optimal difficulty on an individual basis.

In the following the user of the hearing aid system or the method may also be denoted the trainee, thus these terms are interchangeable.

In the following the terms "melodic sequence" and "melody" may also be used interchangeably, thus the term "melody" is to be interpreted very broadly insofar as any sequence of notes from a musical scale may be denoted a melody.

Basically any scale can be used such as e.g.: the diatonic, chromatic, whole tone, pentatonic, octatonic, hexatonic, heptatonic, tritonic, tetratonic and microtonal scales, but also non-western scales such as e.g. the Hejaz, Pelog and Slendro scales, or the swaras of Indian music that may comprise of only five, six or seven tones and may use intervals smaller than a semitone or one of the seventy two different scales of Arabic maqam music.

Further any kind of scale tuning may be used, e.g. tempered or non-tempered scales.

The invention may be implemented as a computer program with a graphical user interface. A set of stimuli (i.e. melodic sequences) is provided for presentation to the trainee. Each set of melodic sequences and corresponding set of trainee responses compose a trial. Each trial is associated with a menu on a graphical user interface that consists of a matrix having a fixed number of squares. In the matrix each square is associated with a unique melodic sequence taken from the set of stimuli. The melodic sequences associated with the squares in each column are interrelated. The melodies associated with the squares in each row are also interrelated. The relation between different melodic sequences in each row or column may include for example: notes having the same pitch, notes having the same temporal duration, same signal processing applied to the melodic sequences, or same progression of the notes in the melodic sequences.

According to a variation the computer program may include self administered tests to determine the musical features to be used during the training. Thus these tests measure the trainee's auditory skills with respect to those musical features.

When the trainee activates a square on the matrix, the trainee will hear a short melodic sequence associated with that square. The trainee first has a possibility to listen to all the melodic sequences in the matrix. The trainee's task is to recognize the inter-relationship between the melodic sequences (the discovery stage). Afterwards, the program removes a number of the squares and places these below the matrix. In the next step (the recognition stage), the trainee has to relocate each of the squares located outside the matrix, in the correct locations inside the matrix.

The trainee's performance is evaluated based on the correctness of the trainee responses and the speed of correct responses during the recognition stage. The set of stimuli used for subsequent trials may be adjusted iteratively based on the trainee's performance to maintain a difficulty level that is challenging to induce improvement in auditory performance of the individual trainee, yet not too difficult to discourage them from continued training. The difficulty of the set of stimuli may be adjusted separately for each adjustable musical feature used in the auditory training.

These and other features of the present invention will become apparent to those skilled in the art from the detailed description wherein the invention will be explained in greater detail.

BRIEF DESCRIPTION OF THE DRAWINGS

FIG. 10 Illustrates different types of responses a trainee can select when attempting to place the square B3 back on the matrix. Bold face font indicates an incorrect response.

FIG. 11 Illustrates the graphical user interface of the test to evaluate a trainee's ability to differentiate melodies of different tempos.

FIG. 12 Illustrates the graphical user interface of the test to evaluate trainees ability to recognize whether melodic sequences are identical.

DETAILED DESCRIPTION

Figure 1:
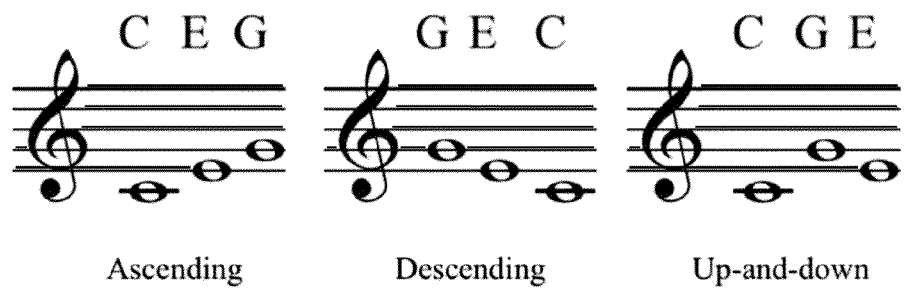
FIG. 1 Illustrates an example of three different melodic sequences having identical notes (C, E, G), but different sequential order of the notes presented acoustically to the user.

The inventors have developed a method and a hearing aid system for auditory training that use musical sounds in a game-like format to provide auditory training for hearing impaired people. The current method is not focused on ear-training typically included as a part of formal musical training targeted to improve listening skills of musicians. Rather, the disclosed method uses music as a stimulus to direct the listeners' attention to auditory events, using processes that may be common for both speech and music. The method is directed at training auditory processing skills that may ultimately enhance speech understanding.

According to variations of the invention, the method of the invention is implemented in a hearing aid system using a computer program running on a smart phone, PDA, tablet computer or any other computing device forming part of the hearing aid system. Preferably the program is running on a tablet computer. The trainee receives the sound from the program, either as an acoustic signal played from the speakers of the training device, or by way of the training device sending the sound as a coded signal via a wireless signal, e.g. using a Bluetooth connection, to the hearing aids or the headset of the trainee which then converts the coded signal to sound.

According to an embodiment of the invention the hearing aid system comprises a graphical user interface, such as a touch screen, for allowing the trainee to investigate and discover how a melody is related to the other melodies in the system, and recognize where the melody fits.

The method of auditory training according to the invention comprises two basic stages: 1) a discovery stage, and 2) a recognition stage. In the discovery stage, the trainee's task is to listen to the melodies embedded in the matrix by activating the squares displayed on the screen. All squares are visually identical, so the trainee can use only auditory cues. The number of repetitions is not limited, to encourage the trainee to listen to the sounds as many times as needed. The trainee's task is to discover the relationships between the melodies within the matrix.

If the hearing aid system comprises a touch screen the individual elements of the matrix will be activated by touch, but obviously any activation means can be used.

Once the trainee has discovered the musical pattern, a variable number of squares are removed from the matrix. The removed squares are positioned on the display outside of the matrix.

According to variations of the embodiments of the invention, any number of squares may be removed from the square, but preferably at least two are removed. Obviously the elements forming the matrix need not be squares but may assume basically any form. In the following the terms "square", "element" and "button" may be used interchangeably to denote the elements forming the matrix.

Furthermore the use of the term "matrix" is not meant to be construed to require that the individual elements together form a square or that the individual elements are aligned in straight rows and columns.

During the recognition stage the trainee's task is to identify which of the squares positioned outside of the matrix correspond to the empty squares in the matrix and to drag-and-drop the squares to their correct locations inside the matrix using the touch screen interface. Once the trainee has recognized each removed square successfully and re-positioned them in the correct positions, then a new matrix with a new set of melodic sequences is provided.

According to a specific variation of the auditory training according to the invention, each trial of the auditory training is associated with a graphical user interface that consists of a display of a square matrix of N×N (N=2, 3, 4, or 5) buttons. Each button is associated with a unique melody ranging from three to seven notes in length. The set of notes used in any given melody are within one octave range. Each melody, while unique, shares one or more musical feature with some of the other melodies. These musical features may include: the notes used in the melody, the temporal duration of the notes, the instruments used to provide the notes, the specific signal processing strategy applied to the melody (e.g. frequency filtering) and rhythm. Additional similarity between melodies can be a specific progression or sequential order of these aforementioned features within the melodies.

Reference is now made to FIG. 1, which illustrates an example of melodic sequences with the same notes but in different sequential order. In FIG. 1 the letter notation commonly used in western music to denote notes is used. The melodic sequence illustrated to the left in FIG. 1 {C, E, G} may be denoted an ascending sequence of tones, whereas the center melodic sequence of FIG. 1 {G, E, C} may be denoted a descending sequence, and the melodic sequence illustrated to the right in FIG. 1 {C, G, E} may be denoted an up-and-down sequence.

Figure 2:
FIG. 2 Illustrates an example of three melodic sequences with a similar sequential order of notes (ascending), but having different notes presented acoustically to the user.

Reference is now made to FIG. 2, which illustrates an example of melody sequences with the same sequential order but comprising different notes including {C, E, G}, {D, F, A}, and {E, F, B}. All these three melodies consist of different notes, but the notes in each melody are in an ascending order.

Figure 3:
FIG. 3 Illustrates an example of three different melodic sequences with an identical rhythm (two shorter notes followed by a longer note), but with a different sequential order of notes and different notes presented acoustically to the user.

Reference is now made to FIG. 3, which illustrates an example of three melody sequences with the same rhythm (i.e. relative duration of the individual notes). Each of these three melodies consists of two equal duration notes followed by a note with twice the duration.

The melodies are assigned within the N×N matrix so that those melodies that share one of the aforementioned musical features occupy the same column or row. For example, melodies on each row could consist of identical notes, while melodies on each column could exhibit the same sequential order of notes.

Figure 4:
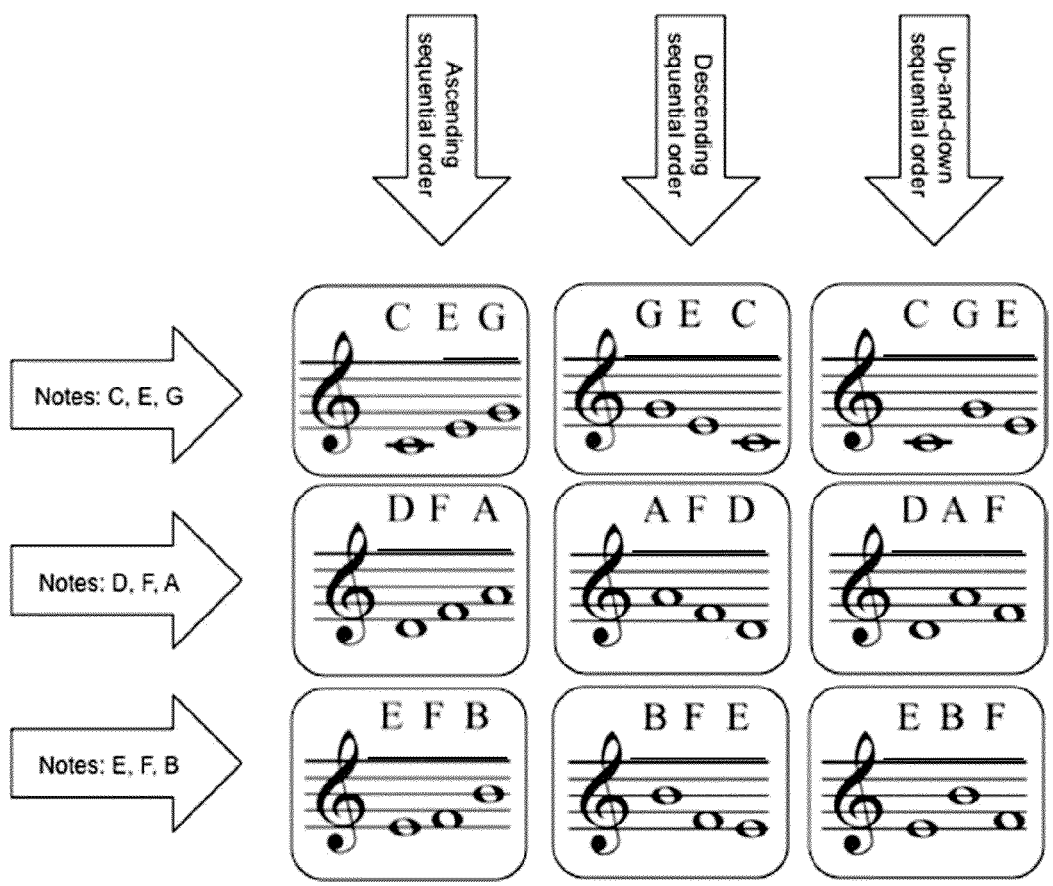
FIG. 4 Illustrates a 3×3 matrix with the notes varying between the rows and the sequence of the notes varying between the columns.

Reference is now made to FIG. 4, which illustrates an example of a 3×3 matrix, wherein the top row has three melodies all comprising the notes C, E, G, but in each column the sequential order of the notes are changed. The same applies to the middle row, having the notes D, E, F, and the bottom row having the notes E, F, B. In this example, the trainee should thus be able to recognize to which row a melody belongs based on the recognition of the same notes. Similarly the vertical system should be recognized based on the sequential order of the notes (ascending, descending or an up-an-down sequential order).

The trainee can utilize at least two strategies in solving each matrix. First, during the discovery stage the trainee can simply try to memorize all the melodies used in the auditory training. Depending on the perceptual similarity between the melodies, this could be a very challenging strategy even for an experienced listener. A more likely approach for most trainees is to first discover the relationship connecting the melodies within the matrix during the discovery stage.

During the recognition state the trainee can compare the candidate melodies positioned outside the matrix against the melodies remaining in the matrix in order to guide the selection. This encourages the trainee to listen attentively, and to compare differences and similarities between different melodies.

The difficulty level of the auditory training at each trial is generally determined by how much the melodies differ. The difficulty is based on the trainee's performance on previous trials. The details of the melodies are defined by the musical features: the notes, the temporal duration of the notes, the types of instruments used to provide the nodes, signal processing applied to the notes, rhythm, and sequential order or the progression of these features within the melodies. The level of detail used for each of the musical features is defined separately and combined when each individual melody is generated.

Figure 5:
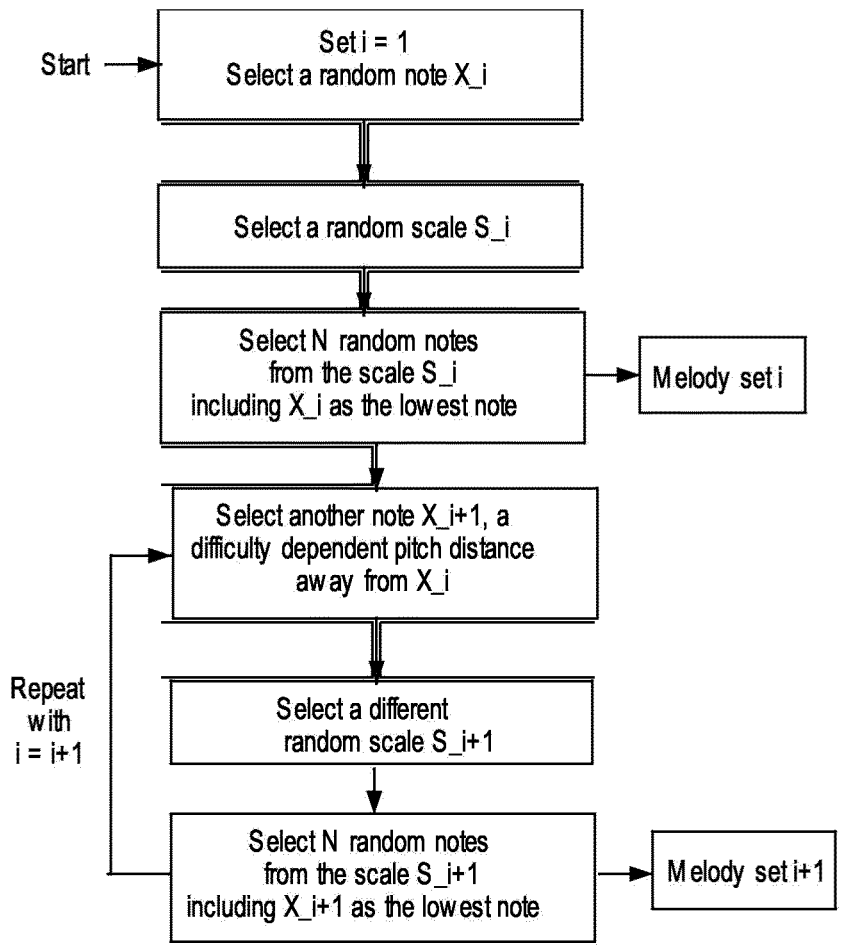
FIG. 5 Illustrates a flowchart of the steps to generate the notes to be used in the melodic sequences.

Reference is now made to FIG. 5, which illustrates a flow chart of how the generation of notes for different melodies with N notes is provided according to an embodiment of the invention. In the first step, a random note X1 is selected from a predetermined range. The frequency range of candidate notes can be restricted for trainees depending on the extent of their hearing loss. Next, a random scale S1 is selected and N−1 additional notes are selected randomly based on the selected scale S1 and with X1 as the lowest note (which in modern western music may be denoted the tonic).

The notes in the second set are selected based on the first set of notes. First, we select a note X2 at a predetermined pitch distance away from X1. The pitch distance, which determines the similarity between transposed melodies, depends on the difficulty level. Also, a new scale type S2 is selected. The scale defines the interval relations between the notes, and the selection of S2 therefore depends on the size of the intervals we want to have in the melody. The size of the intervals is determined by the difficulty level. The N notes of the second set are selected such that X2 is the lowest note (the tonic) and such that the same scale degrees, as were used in the generation of the first set, are used. The sets of notes used to provide further melodies are generated by repeating the above steps.

Figure 6:
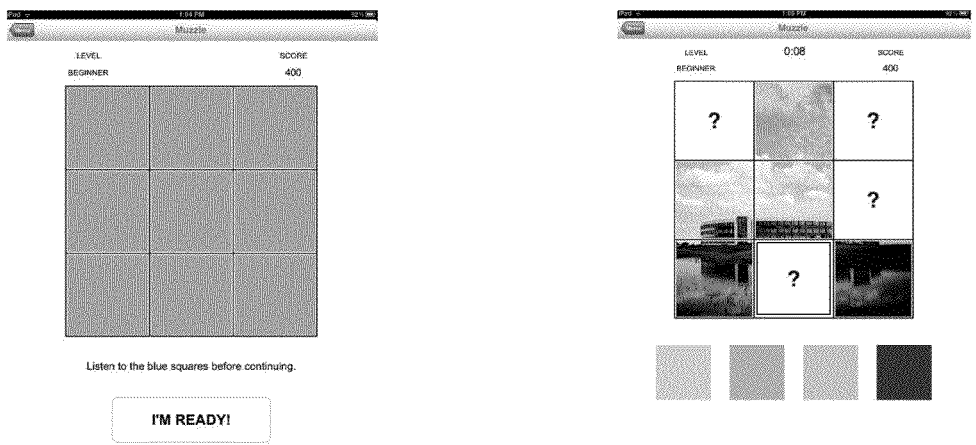
FIG. 6 Illustrates on the left a menu of a graphical user interface of the discovery stage, where the user can listen to the melodic sequences associated with the squares of the matrix, and on the right the recognition stage, where a number of squares of the matrix have been removed and placed below the matrix.

Reference is now made to FIG. 6, which illustrates on the left a menu of a graphical user interface of the discovery stage, where the user can listen to the melodic sequences associated with the squares of the matrix, and on the right the recognition stage, where a number of squares of the matrix have been removed and placed below the matrix.

The difficulty of the auditory training is adjusted iteratively for each trial based on the trainee's performance. The adaptive difficulty provides training materials that are challenging enough to maintain trainee's interest and attention but not so difficult as to induce fatigue or frustration. If the trainee solves the matrix without any incorrect entries the difficulty level is raised. If the trainee enters two or more incorrect responses the difficulty level is lowered. If the trainee enters one incorrect response the difficulty level is maintained at the current level.

The difficulty of each matrix is defined by the size of the matrix, the perceptual similarity of melodies, the length of the melody sequences, and the number of squares removed after the discovery stage. The perceptual similarity between melodies is approximated using e.g. the pitch distance between the lowest notes of the melodies and using the temporal similarity between the melodies. The "temporal similarity" between melodies is defined by how similar the tempo, the rhythm and the relative temporal durations of the individual notes in different melodies are.

The perceptual similarities of melodies along the two auditory dimensions frequency and duration are controlled independently. The independent adjustment for different auditory dimensions allows the difficulty of the training to be tailored to specific listening challenges of the individual trainee. In addition to the adaptive difficulty of the auditory training, another tool, aimed at encouraging continued use of the training program, is a scoring system. During the recognition state the trainee is given a numerical score to track own performance and to motivate for improvement. The score for each level is based on three factors: time for each correct response, difficulty level, and number of incorrect responses. At the termination of each training trial, the trainee can compare her/his current score against the previous best performance score.

We will describe the method of adjusting the similarity of the melodies for different musical features independently here using a formal description first, and then illustrate the method through an example.

Figure 7:
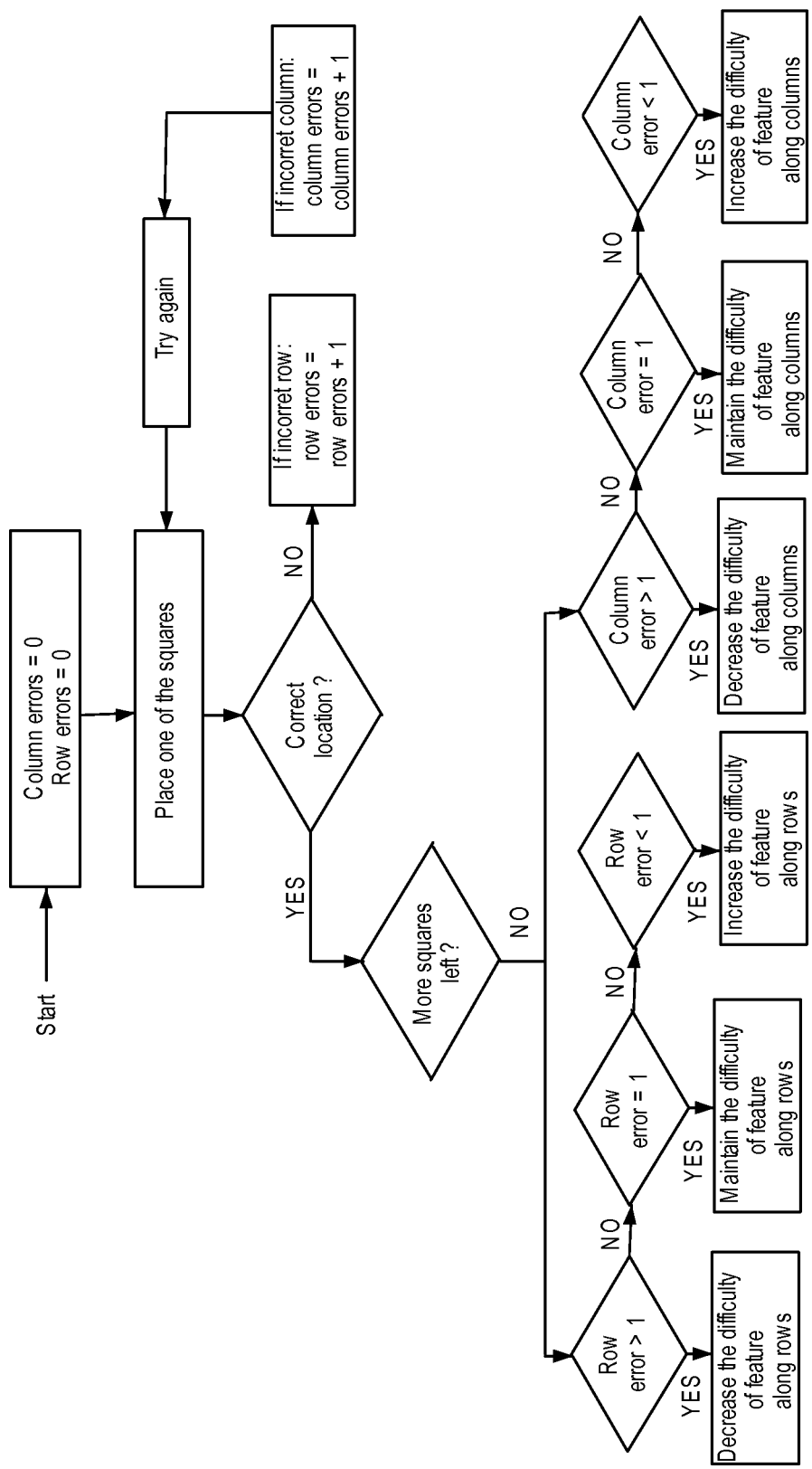
FIG. 7 Illustrates a flowchart demonstrating the method that allows each musical feature to be adjusted independently based on an individual trainee's performance.

The flowchart illustrating the operation of the method to adjust the perceptual similarity is given in FIG. 7. When the trainee places one of the missing squares on one of the empty locations on the matrix, the method checks whether the square was placed in the correct row and in the correct column separately. Any misplacements are called "row error" or "column error" respectively. If the square was placed in an incorrect row the number of "row errors" is increased. If the square was placed in an incorrect column the number of "column errors" is increased. Once the trainee has completed the matrix by placing all squares in their correct locations, the trial terminates. The level of similarity or difficulty for the next trial is based on "row error" and "column error" counts. If the trainee does not commit any "row errors", the difficulty level of the melodic sequences along the rows is increased (perceptual similarity decreased). If the trainee commits a single "row error", the difficulty is kept at the same level. If the trainee commits more than one "row error", the difficulty level along the rows is decreased (perceptual similarity increased). The difficulty level of the melodic sequences along the columns is treated similarly.

The musical features that define the rows and columns of each matrix are determined on a trial-by-trial basis. The features are randomly selected from the set of possible features. The set of possible features can either be fixed or may be customized based on the individual needs of a trainee.

The auditory training program includes two self administered tests to determine which musical features are included in the customized set of possible features used during the training. These tests measure the trainee's auditory skills with respect to the adjustable musical features that can be used during the training.

The first test measures the trainee's ability to distinguish between melodies of different tempos. The tempo refers to the absolute temporal duration of notes used in the melodies. The test uses two-interval forced choice (2IFC) method to determine the just-noticeable-difference (JND) in tempo between two otherwise identical melodies. The basic components of the task are:

two melodies with different tempos are presented sequentially with a 0.5 second silence between the melodies;

the trainee indicates which of the two melodies was slower in tempo (see FIG. 11);

the tempo difference between the two melodies is adjusted based on the response.

The adjustment is done using the two-up one-down staircase procedure explained in a paper by Levitt (1971) "Transformed up-down methods in psychoacoustics" *J Acoust Soc Am* 49(2):467-477. The initial tempo difference is 40 beats per minute (bpm) (e.g. 100 bpm vs 60 bpm.). The adjustment step size in tempo is 15 bpm initially, 10 bpm after the first reversal, 4 bpm after the second reversal, and 1 bpm after the third reversal. A termination rule of five reversals is used.

The second test requires identification of pitches. This test measures the trainee's auditory memory span for a sequence of musical notes of different pitches. The test stimuli consist of melodies with a variable number of notes with different pitch values. The test uses two-interval adjustment matrix (TIAM) adapted from a single interval adjustment matrix procedure explained in a paper by Kaernbach (1990) "A single interval adjustment-matrix (SIAM) procedure for unbiased adaptive testing" J Acoust Soc Am. 88(6):2645-55, in order to determine the number of notes in a melody that the trainee can memorize.

The basic components of the task are:

two melodies are presented sequentially with a 0.5 second silence between the melodies. The two melodies are either identical, or the sequential locations of two notes are interchanged in one of the otherwise identical melodies. The likelihood of the two melodies being identical is 50% and conversely the likelihood of the two melodies being different is also 50%.

The trainee indicates if the two melodies were different or identical using a graphical user interface on the tablet computer (see FIG. 12).

The number of notes in the next pair of stimuli is adjusted based on the response and the stimuli condition. The trainee responses can be classified into one of the four categories: hit (i.e. it is correctly assessed that the melodies are the same), miss (i.e. it is wrongly assessed that the melodies are the same), false alarm (i.e. it is wrongly assessed that the melodies are different), and correct rejection (i.e. it is correctly assessed that the melodies are different). In the event of a hit, the length of the melodies is increased by one. In the event of a miss, the length of the melodies is decreased by one. In the event of a false alarm, the length of the melodies is reduced by two notes. In the event of a correct rejection the length of the melodies is not changed. The termination rule of the test is set to five reversals.

The trainees listening skills with respect to any of the other musical features that can be included in the auditory training (e.g. frequency filtering) may also be tested using one of the two methods described above.

Figure 8:
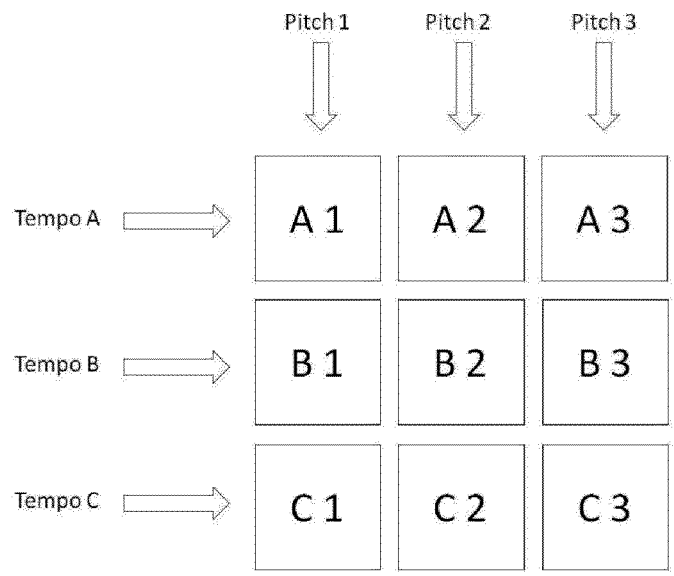
FIG. 8 Illustrates an example of a 3×3 game board for auditory training that includes two musical features that are varied: "pitch" and "tempo". Each row includes a unique tempo, while each column includes a unique set of pitches.

We will use the following example to simplify the description of a method according to an embodiment of the invention. Assume a method of auditory training based on using a 3×3 matrix. Also, assume that the two musical features that the program will vary are the pitch of the notes (frequency dimension), and the tempo of the melodies. Let us call these two features "pitch" and "tempo" respectively. The "pitch" feature has three variants labeled: "1", "2", and "3". The "tempo" feature has three variants labeled: "A", "B", and "C". Let us further assume that the "pitch" feature is varied along the columns of the game board, and the "tempo" feature is varied along the rows of the game board (see FIG. 8). The trainee does not see the labels shown in FIG. 8. These labels were included in this description solely to illustrate how the method works.

Figure 9:
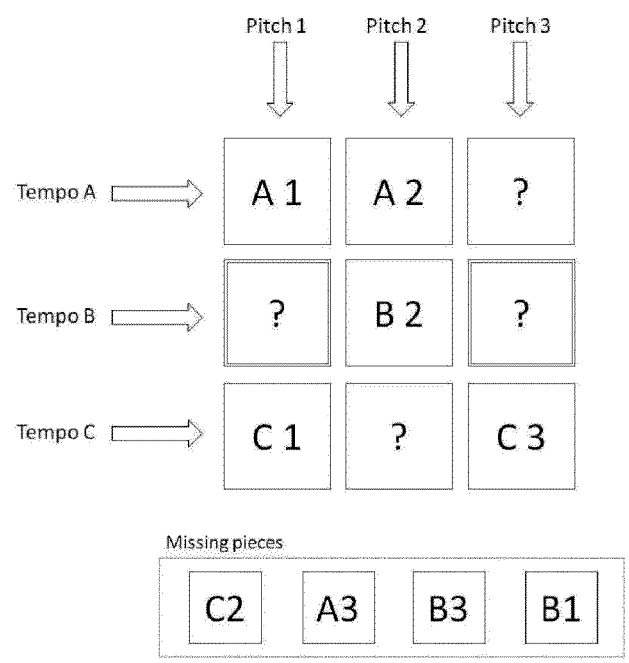
FIG. 9 Illustrates an example of a 3×3 game board for auditory training with four squares placed outside the matrix. Removed squares are A3, B1, B3, and C2.

In the recognition stage of the auditory training, some of the squares are removed from the matrix. The trainee's task is to drag the removed squares to their correct original locations. Let us assume a game-board with four squares removed as displayed in FIG. 9. In this example the four removed squares that the trainee needs to position back to the matrix were A3, B1, B3, and C2.

In this example, the trainee can attempt to position each missing piece in one of the four empty locations on the game board labeled with "?". Each time the trainee places one of the removed squares on the game board there are two options: the square was placed in a correct position or the square was placed in an incorrect position. When the square is placed in an incorrect position three scenarios are possible:

the square is placed in an incorrect row but in a correct column;

the square is placed in a correct row but in an incorrect column; or the square is placed in an incorrect row and in an incorrect column.

FIG. 10 illustrates all the possibilities where the piece B3 can be placed in the illustrated trial. The incorrect row and column locations are indicated with bold face font. The figure demonstrates that when the piece B3 is placed in the location A3 the "pitch" is correct but the "tempo" is incorrect. When the piece B3 is placed in the location B1 the "tempo" is correct but the "pitch" is incorrect. When the piece B3 is placed in the location C2 both the "pitch" and "tempo" are incorrect.

Table 1 lists all the possible combinations of user actions for all game pieces in this example.

TABLE 1

All the possible responses that the trainee can give in the trial described in the text

| Removed square | Where trainee placed the square | "Pitch error" | "Tempo error" | No errors |
|---|---|---|---|---|
| A3 | A3 |   |   | X |
|   | B1 | X | X |   |
|   | B3 |   | X |   |
|   | C2 | X | X |   |
| B1 | A3 | X | X |   |
|   | B1 |   |   | X |
|   | B3 | X |   |   |
|   | C2 | X | X |   |
| B3 | A3 |   | X |   |
|   | B1 | X |   |   |
|   | B3 |   |   | X |
|   | C2 | X | X |   |
| C2 | A3 | X | X |   |
|   | B1 | X | X |   |
|   | B3 | X | X |   |
|   | C2 |   |   | X |

Table 2 summarizes all the possible actions that are carried out based on the number of "row errors" and "column errors".

TABLE 2

Possible actions based on error types

| Error count | Action |
|---|---|
| Row errors = 0 | Increase the difficulty of musical feature along row dimension (i.e. decrease perceptual similarity) |
| Row errors = 1 | Retain the difficulty of musical feature along row dimension |
| Row errors > 1 | Decrease the difficulty of musical feature along row dimension (i.e. increase perceptual similarity) |
| Column errors = 0 | Increase the difficulty of musical feature along column dimension (i.e. decrease perceptual similarity) |
| Column errors = 1 | Retain the difficulty of musical feature along column dimension |
| Column errors > 1 | Decrease the difficulty of musical feature along column dimension (i.e. increase perceptual similarity) |

The difficulty level of the training is adjusted iteratively based on the trainee's skills. The difficulty level may be adjusted by varying the size of the matrix, by adjusting the number of individual notes in the melodies, and by adjusting the number of items removed from the matrix prior to the recognition stage. The difficulty level in one embodiment can be defined as the lowest difficulty level of the two musical features used in the matrix at any given time.

Table 3 demonstrates how the level of the training may be adjusted, according to an embodiment, for the first 25 levels.

TABLE 3

An example of how the difficulty of the training program can be adjusted based on the difficulty level

| Difficulty level | Matrix size | Number of individual notes in each melody | Number of items removed |
|---|---|---|---|
| 1 | 3 × 3 | 3 | 4 |
| 2 | 3 × 3 | 3 | 4 |
| 3 | 3 × 3 | 3 | 5 |
| 4 | 3 × 3 | 3 | 5 |
| 5 | 3 × 3 | 3 | 5 |
| 6 | 3 × 3 | 3 | 5 |
| 7 | 3 × 3 | 3 | 5 |
| 8 | 3 × 3 | 4 | 6 |
| 9 | 3 × 3 | 4 | 6 |
| 10 | 3 × 3 | 4 | 6 |
| 11 | 3 × 3 | 4 | 6 |
| 12 | 3 × 3 | 4 | 6 |
| 13 | 4 × 4 | 3 | 7 |
| 14 | 4 × 4 | 3 | 7 |
| 15 | 4 × 4 | 3 | 7 |
| 16 | 4 × 4 | 3 | 7 |
| 17 | 4 × 4 | 4 | 8 |
| 18 | 4 × 4 | 4 | 8 |
| 19 | 4 × 4 | 4 | 8 |
| 20 | 4 × 4 | 4 | 8 |
| 21 | 4 × 4 | 4 | 8 |
| 22 | 4 × 4 | 4 | 8 |
| 23 | 4 × 4 | 4 | 8 |
| 24 | 4 × 4 | 4 | 8 |
| 25 | 4 × 4 | 4 | 8 |

During the recognition state the trainee is given a numerical score to track own performance and to motivate for improvement. The score for each level is based on three factors: time for each correct response, difficulty level, and number of incorrect responses.

Table 4 shows the increment in score for each individual correct response as a function of the time and the number of errors committed according to an embodiment of the method of auditory training.

TABLE 4

Increment in score for each individual correct response as a function of the time and the number of errors committed

| | | Time | | | | | | | |
|---|---|---|---|---|---|---|---|---|---|
| | | <10 sec | <20 sec | <30 sec | <40 sec | <50 sec | <60 sec | <70 sec | >70 sec |
| Number of errors | 0 | 100 | 90 | 80 | 70 | 60 | 50 | 40 | 10 |
| | 1 | 90 | 81 | 72 | 63 | 54 | 45 | 36 | 9 |
| | 2 | 80 | 72 | 64 | 56 | 48 | 40 | 32 | 8 |
| | 3 | 70 | 63 | 56 | 49 | 42 | 35 | 38 | 7 |
| | 4 | 60 | 54 | 48 | 42 | 36 | 30 | 24 | 6 |
| | 5 | 50 | 45 | 40 | 35 | 30 | 25 | 20 | 5 |
| | 6 | 40 | 36 | 32 | 28 | 24 | 20 | 16 | 4 |
| | 7 | 30 | 27 | 24 | 21 | 18 | 15 | 12 | 3 |
| | 8 | 20 | 18 | 16 | 14 | 12 | 10 | 8 | 2 |

According to a variation of the embodiment of the invention, the matrix used in the auditory training may consist initially of only three boxes arranged graphically to form a sequential order, e.g. in a row or a column.

Having only three boxes, either at least two of the original three boxes need to be moved away from the matrix in order to provide the user of the auditory training with at least two options to choose between when re-arranging the boxes or only one of the three original boxes is moved away from the matrix and a fourth box is added outside of the matrix whereby the user of the auditory training is provided with at least two options to choose between when re-arranging the boxes.

According to yet other variations, no boxes are moved away from the matrix, instead the matrix is formed initially with empty spaces that require boxes, that initially are positioned outside of the matrix to be re-arranged in order to fill these empty spaces. In its most simple form the matrix initially consists of only two boxes arranged sequentially and sharing a musical feature and two additional boxes wherein only one of the additional boxes shares the musical feature.

According to still another variation a first graphical user interface illustrates in one part of the interface at least one melody and an indication of a musical relationship, and in another part of the interface, the user is provided with the option to choose from a number of melodies, wherein at least one melody fits the indicated musical relationship.

Figure 13:
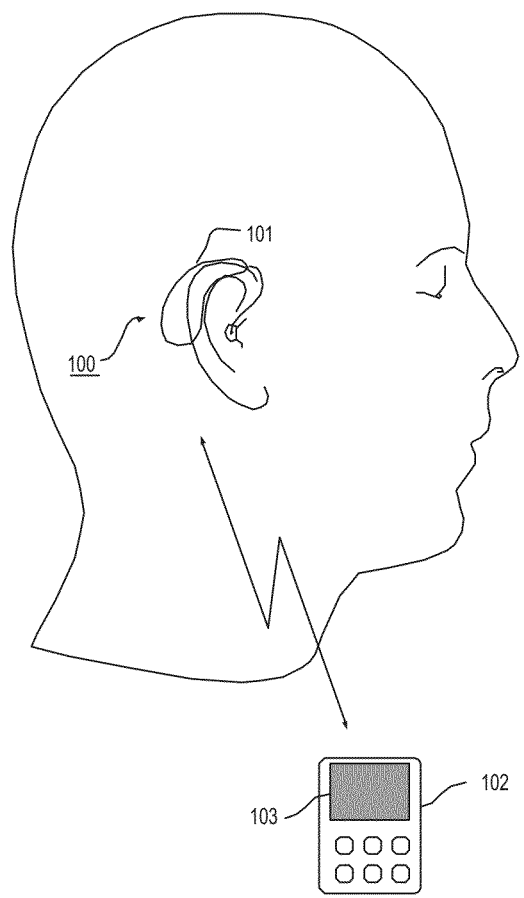
FIG. 13 Illustrates a hearing aid system according to an embodiment of the invention.

Reference is now made to FIG. 13, which illustrates a hearing aid system 100 according to an embodiment of the invention. The hearing aid system 100 is configured to carry out any of the methods of auditory training disclosed in the present application. The hearing aid system 100 comprises a hearing aid 101 and an auxiliary device in the form of a remote control or smart phone 102 with display 103. The hearing aid 101 is adapted to play sound signals for the user, as controlled by auditory training software.

According to a variation of the embodiment of FIG. 13, the method of auditory training is implemented as a computer software program (a so called "app") that may be downloaded by a smart phone or a tablet computer, wherein the app is adapted to provide the acoustical output of the auditory training (i.e. the melodies) to the user of the hearing aid system by transmitting the digital signals representing the acoustical output from the smart phone or table computer and to a hearing aid and using the hearing aid to convert the digital signals to sound that the hearing aid system user can perceive. The app is further adapted to provide visual feedback using the display 103. The display is preferably a touch screen, by which the user can control the training and provide feedback. The user interface comprises audio feedback by the hearing aid, and visual feedback and control input on the display.

We claim:

1. A method of auditory training, comprising the steps of:
providing in a graphical user interface a first arrangement comprising a first, second and third box positioned at a first, second and third location respectively,
wherein said graphical user interface is adapted to enable a user to activate a box, to launch the playing of an auditory sequence of notes from a musical scale, and
wherein said graphical user interface is adapted to enable a user to select, and move and drop a box,
prompting the user to re-arrange the location of at least one box,
wherein said first, second and third boxes are configured such that they share a musical characteristic, wherein said musical characteristic is selected from a group comprising the selected notes from a musical scale, the type of instrument used to provide the notes, the sequential order of the notes and the duration of the notes, and
wherein the graphical appearance of said boxes is adapted such that re-arrangement by the user will require the user to activate said boxes, and listen to the provided auditory sequences to identify sound patterns distinguishing the boxes, to consider similarities of the sound patterns and to move a box into a position where the sound pattern of the box shares similarities with the sound patterns of the neighboring boxes.

2. The method according to claim 1, comprising the step of:
providing a second arrangement of said boxes in the graphical user interface, prior to prompting the user to re-arrange,
wherein at least one of said first, second and third boxes have been moved away from a first location and to a second location, hereby leaving an empty space at said first location.

3. The method according to claim 2, wherein an additional box has been added to a fifth location.

4. The method according to claim 1, wherein said first arrangement of boxes provided by the graphical user interface comprises between 6 and 64 boxes arranged in a matrix like structure.

5. The method according to claim 4, wherein the boxes of said first arrangement are configured such that they share a first musical characteristic along the rows of the matrix like structure and such that they share a second musical characteristic along the columns of the matrix like structure.

6. The method according to claim 1 comprising the step of:
evaluating the response of the user to said prompting.

7. The method according to claim 6, comprising the step of:
adjusting the difficulty level of the auditory training based on the user response.

8. The method according to claim 6, comprising the step of:
providing feedback to the user, with respect to how successful the auditory training has been, based on an evaluation of the user responses.

9. The method according to claim 1, comprising the step of:
providing feedback to the user as to whether the box has been moved to the correct position.

10. The method according to claim 1 wherein said method is executed by a hearing aid system.

11. A hearing aid system comprising a hearing aid and a graphical user interface, said graphical user interface providing a first arrangement comprising a first, second and third box positioned at a first, second and third location respectively,
wherein said graphical user interface is adapted to enable a user to activate a box to launch the playing by said hearing aid of a respective auditory sequence of notes from a musical scale,
wherein said graphical user interface is adapted to enable a user to select, and move and drop a box,
wherein each of said first, second and third boxes is associated with a particular auditory sequence, the respective auditory sequences being distinguished, yet sharing some musical characteristics, in order to suggest to the user a meaningful ranking among the boxes in accordance with the auditory sequences, said musical characteristics being selected from a group comprising selected notes from a musical scale, type of musical instrument used to provide the notes, sequential order of the notes and duration of the notes, and
wherein the graphical user interface is adapted to prompt the user to activate said boxes to play respective auditory sequences, to listen to the auditory sequences, to compare sound patterns of respective auditory sequences and consider rankings among them, and to move at least one box into a position where auditory sequences of neighboring boxes together provide a meaningful pattern.

12. The hearing aid system according to claim 11, comprising at least one hearing aid and an auxiliary device selected from the group comprising at least a hearing aid remote control, a smart phone, a tablet computer and a personal digital assistant.

13. A non-transitory computer-readable storage medium carrying computer-executable instructions, which when executed in a personal communication device provides auditory training of a hearing impaired person, according to a method comprising the steps of:
providing in a graphical user interface a first arrangement comprising a first, second and third box positioned at a first, second and third location respectively, wherein said graphical user interface is adapted to enable a user to activate a box, to launch the playing of an auditory sequence of notes from a musical scale, and wherein said graphical user interface is adapted to enable a user to select, and move and drop a box, prompting the user to re-arrange the location of at least one box, wherein said first, second and third boxes are configured such that they share a musical characteristic, wherein said musical characteristic is selected from a group comprising the selected notes from a musical scale, the type of instrument used to provide the notes, the sequential order of the notes and the duration of the notes, and wherein the graphical appearance of said boxes is adapted such that re-arrangement by the user will require the user to activate said boxes, and listen to the provided auditory sequences to identify sound patterns distinguishing the boxes, to consider similarities of the sound patterns and to move a box into a position where the sound pattern of the box shares similarities with the sound patterns of the neighboring boxes.

14. The non-transitory computer-readable storage medium according to claim 13, wherein interaction with a hearing aid is provided by adapting the computer-readable storage medium to provide the acoustical output of the auditory training to a user of said hearing aid by using an electrical-acoustical output transducer of the hearing aid to provide sound to said hearing impaired person.

\* \* \* \* \*